United States Patent
Potlapally et al.

(10) Patent No.: US 8,377,950 B2
(45) Date of Patent: Feb. 19, 2013

(54) CRYSTALLINE FORM OF 5-[4-[[3-METHYL-4-OXO-3,4-DIHYDROQUINAZOLIN-2-YL]METHOXY]BENZYL]THIAZOLIDINE-2,4-DIONE POTASSIUM SALT

(75) Inventors: Rajender Kumar Potlapally, Hyderabad (IN); Raju Srisilla, Hyderabad (IN); Ramabhadra Sarma Mamillapalli, Hyderabad (IN); Om Reddy Gaddam, Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 0 days.

(21) Appl. No.: 10/507,399

(22) PCT Filed: Mar. 14, 2003

(86) PCT No.: PCT/IB03/00935
§ 371 (c)(1),
(2), (4) Date: Jun. 13, 2005

(87) PCT Pub. No.: WO03/078425
PCT Pub. Date: Sep. 25, 2003

(65) Prior Publication Data
US 2005/0234079 A1    Oct. 20, 2005

(30) Foreign Application Priority Data
Mar. 15, 2004    (IN) .............................. 180/MAS/2002

(51) Int. Cl.
*A01N 43/54*    (2006.01)
*A61K 31/517*    (2006.01)
(52) U.S. Cl. .................................... 514/266.2; 544/287
(58) Field of Classification Search ............... 514/266.2; 544/284
See application file for complete search history.

(56) References Cited

FOREIGN PATENT DOCUMENTS
WO    97-41097    * 11/1997
WO    00/15638    * 3/2000

OTHER PUBLICATIONS

Thermo Fisher Sci. Inc., Copy right 2001-2006. pp. 1-3.*
Gu, C-H et. al., "Polymorph Screening: Influence of Solvents on the Rate of Solvent-Mediated Polymorphic Transformation", J. of Pharm. Sci., Nov. 2001, vol. 90, No. 1, pp. 1878-1890.*
Rouhi, A. Maureen, "The Right Stuff", Chemical and Engineering News, 2003, 81 (8), p. 32-35.
Gavezzotti, Angelo, "Are Crystal Structures Predictable?", Acc. Chem. Res., 1994, 27, 309-314.
Gavezzotti, Angelo, "Ten Years of experience in polymorph prediction: what next?", CrystEngComm, 2002, 4(61), 343-347.
Graeme M. Day, et al. (2006) "Investigating the latent polymorphism of maleic acid", Chemical Communications 1 (1): 54-56.
Thallapally PK, et al., (2004). "Polymorphism of 1,3,5-trinitrobenzene induced by a trisindane additive", Angewandte Chemie International Edition, 43 (9): 1149-1155.

* cited by examiner

*Primary Examiner* — James O Wilson
*Assistant Examiner* — Alexander R Pagano
(74) *Attorney, Agent, or Firm* — Gilman Pergament LLP (57) ABSTRACT

The present invention relates to novel crystalline Form of 5-[4-[[3-methyl-4-oxo-3,4-dihydroquinazolin-2-yl]methoxy]benzyl]thiazolidine-2,4-dione potassium salt having the formula (I). The invention also relates to a pharmaceutical composition comprising the novel crystalline Form and a pharmaceutically acceptable carrier. The novel crystalline Form of the present invention is more active, as an antidiabetic agent than the hitherto known 5-[4-[[3-methyl-4-oxo-3,4-dihydroquinazolin-2-yl]methoxy]benzyl]thiazolidine-2,4-dione potassium salt.

(I)

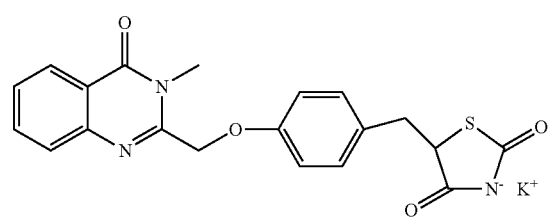

4 Claims, 6 Drawing Sheets

CRYSTALLINE FORM OF 5-[4-[[3-METHYL-4-OXO-3,4-DIHYDROQUINAZOLIN-2-YL]METHOXY]BENZYL]THIAZOLIDINE-2,4-DIONE POTASSIUM SALT

FIELD OF THE INVENTION

The present invention relates to novel crystalline Form of 5-[4-[[3-methyl-4-oxo-3,4-dihydroquinazolin-2-yl]methoxy]benzyl]thiazolidine-2,4-dione potassium salt having the formula (I). The invention also relates to a pharmaceutical composition comprising the novel crystalline Form and a pharmaceutically acceptable carrier. The novel crystalline Form of the present invention is more active, as an antidiabetic agent than the hitherto known 5-[4-[[3-methyl-4-oxo-3,4-dihydroquinazolin-2-yl]methoxy]benzyl]thiazolidine-2,4-dione potassium salt (I)

The present invention also relates to a process for the preparation of novel crystalline Form of 5-[4-[[3-methyl-4-oxo-3,4-dihydroquinazolin-2-yl]methoxy]benzyl]thiazolidine-2,4-dione potassium salt, having the formula (I).

The novel crystalline Form of 5-[4-[[3-methyl-4-oxo-3,4-dihydroquinazolin-2-yl]methoxy]benzyl]thiazolidine-2,4-dione potassium salt, of formula (I) defined above of the present invention reduce blood glucose and has beneficial effect on coronary heart disease and atherosclerosis.

Out of the many drugs available for the treatment of diabetic ailments, the thiazolidinedione derivatives are very prominent and are considered as much superior effective constituents compared to the sulphonyl ureas. 5-[4-[[3-methyl-4-oxo-3,4-dihydroquinazolin-2-yl]methoxy]benzyl]thiazolidine-2,4-dione potassium salt, one such thiazolidinedione which exhibited euglycemic effect, was reported in our U.S. Pat. No. 5,985,884.

The novel crystalline Form of 5-[4-[[3-methyl-4-oxo-3,4-dihydroquinazolin-2-yl]benzyl]thiazolidine-2,4-dione potassium salt, of formula (I) is useful in reducing body weight and for the treatment and/or prophylaxis of diseases such as hypertension, coronary heart disease, atherosclerosis, stroke, peripheral vascular diseases and related disorders. The novel crystalline Form of 5-[4-[[3-methyl-4-oxo-3,4-dihydroquinazolin-2-yl]benzyl]thiazolidine-2,4-dione potassium salt, of formula (I) can be used for the treatment of certain renal diseases including glomerulonephritis, glomerulosclerosis, nephrotic syndrome, hypertensive nephrosclerosis and nephropathy. The novel crystalline Form of 5-[4-[[3-methyl-4-oxo-3,4-dihydroquinazolin-2-yl]methoxy]benzyl]thiazolidine-2,4-dione potassium salt, of formula (I) is also useful for the treatment and/or prophylaxis of insulin resistance (type II diabetes), leptin resistance, impaired glucose tolerance, dyslipidemia, disorders related to syndrome X such as hypertension, obesity, insulin resistance, coronary heart disease and other cardiovascular disorders. The novel crystalline Form of 5-[4-[[3-methyl-4-oxo-3,4-dihydroquinazolin-2-yl]methoxy]benzyl]thiazolidine-2,4-dione potassium salt of formula (I) may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, inflammation and for the treatment of cancer. The novel crystalline Form of 5-[4-[[3-methyl-4-oxo-3,4-dihydroquinazolin-2-yl]benzyl]thiazolidine-2,4-dione potassium salt, of formula (I) of the present invention is useful in the treatment and/or prophylaxis of the above said diseases in combination/con-comittant with one or more HMG CoA reductase inhibitors, hypolipidemic/hypolipoproteinemic agents such as fibric acid derivatives, nicotinic acid, cholestyramine, colestipol, probucol.

BACKGROUND OF THE INVENTION

The latest trend that has, of late, crept into the pharmaceutical industry is the studies on polymorphism in drugs and the difference in the activity of different polymorphic forms of a given drug. By the term polymorphism we mean to include different physical forms, crystal forms, crystalline/liquid crystalline/non-crystalline (amorphous) forms. This has especially become very interesting after observing that many antibiotics, antibacterials, tranquilizers etc., exhibit polymorphism and some/one of the polymorphic forms of a given drug exhibit superior bio-availability and consequently show much higher activity compared to other polymorphs. Sertraline, Frentizole, Ranitidine, Sulfathiazole, Indomethacine etc. are some of the important examples of pharmaceuticals, which exhibit polymorphism. Polymorphism in drugs is a topic of current interest and is evident from the host of patents being granted. To cite a few, U.S. Pat. No. 5,700,820 discloses six polymorphic forms of Troglitazone, U.S. Pat. No. 5,248,699 discusses about five polymorphic forms of Sertraline hydrochloride while EP 014590 describes four polymorphic forms of Frentizole. EP 490648 and EP 022527 also deal with the subject of polymorphism in drugs.

Several references discloses the structure of 5-[4-[[3-methyl-4-oxo-3,4-dihydroquinazolin-2-yl]methoxy]benzyl]thiazolidine-2,4-dione potassium salt but no such reference touch upon the possibility/observation that 5-[4-[[3-methyl-4-oxo-3,4-dihydroquinazolin-2-yl]methoxy]benzyl]thiazolidine-2,4-dione potassium salt exists in different polymorphic Forms. There is no published literature regarding such an observation till date. Polymorphism in drugs is a topic of current interest and is evident from the host of patents being granted to cite a few U.S. Pat. No. 5,248,699 discusses about five polymorphic forms of Sertraline hydrochloride while EP 014590, describes four polymorphic forms of Frentizole EP 490648 and EP 022527, six polymorphic forms of Troglitazone WO 97/27191 also deal with the subject of polymorphism in drugs. The fact that polymorphism in 5-[4-[[3-Methyl-4-oxo-3,4-dihydroquinazolin-2-yl]methoxy]benzyl]thiazolidine-2,4-dione potassium salt has not been studied earlier coupled with the current interest in the field of polymorphism in drugs prompted us to take-up this investigation. Our observations and results form the subject matter of the present invention.

With a view to prevent/cure the chronic complications of diabetes, research is being conducted round the world in recent times. 5-[4-[[3-methyl-4-oxo-3,4-dihydroquinazolin-2-yl]methoxy]benzyl]thiazolidine-2,4-dione potassium salt is being considered as one of the effective anti-diabetic drugs having multi-purpose activity not only acting on diabetes itself but also on the reduction of the triglycerides and also on the accompanying complications mentioned above. Indeed the said 5-[4-[[3-methyl-4-oxo-3,4-dihydroquinazolin-2-yl] methoxy]benzyl]thiazolidine-2,4-dione potassium salt is under development for the treatment of diabetes and related disorders.

SUMMARY OF THE INVENTION

With an objective to develop novel polymorphic forms for lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetes complications thereof, for the treatment of diseases wherein insulin resistance is the pathophysiological mechanism and for the treatment of hypertension, with better efficacy, potency and lower toxicity, we focussed our research to develop new polymorphic forms effective in the treatment of the above mentioned diseases. Effort in this direction has led to polymorphic forms having the formula (I).

Another objective of the present invention is to provide novel crystalline Form of 5-[4-[[3-methyl-4-oxo-3,4-dihydroquinazolin-2-yl]benzyl]thiazolidine-2,4-dione potassium salt, their stereoisomers, their pharmaceutically acceptable solvates and pharmaceutical compositions containing them or their mixtures which may have agonist activity against PPARα and/or PPARγ, and optionally inhibit HMG CoA reductase, in addition to having agonist activity against PPARα and/or PPARγ.

Another objective of the present invention is to provide novel crystalline Form of 5-[4-[[3-methyl-4-oxo-3,4-dihydroquinazolin-2-yl]benzyl]thiazolidine-2,4-dione potassium salt, their stereoisomers, pharmaceutically acceptable solvates and pharmaceutical compositions containing them or their mixtures having enhanced activities, without toxic effect or with reduced toxic effect.

Yet another objective of the present invention is to provide a process for the preparation of novel crystalline Form of 5-[4-[[3-methyl-4-oxo-3,4-dihydroquinazolin-2-yl]benzyl] thiazolidine-2,4-dione potassium salt, their stereoisomers, pharmaceutically acceptable solvates.

Still another objective of the present invention is to provide pharmaceutical compositions containing novel crystalline Form of 5-[4-[[3-methyl-4-oxo-3,4-dihydroquinazolin-2-yl] methoxy]benzyl]thiazolidine-2,4-dione potassium salt, solvates or their mixtures in combination with suitable carriers, solvents, diluents and other media normally employed in preparing such compositions.

In our efforts to prepare new polymorph, 5-[4-[[3-methyl-4-oxo-3,4-dihydroquinazolin-2-yl]methoxy]benzyl]thiazolidine-2,4-dione potassium salt is prepared in acetonitrile xylene mixture from 5-[4-[[3-methyl-4-oxo-3,4-dihydroquinazolin-2-yl]methoxy]benzyl]thiazolidine-2,4-dione and potassium tertiary butoxide.

BRIEF DESCRIPTION OF THE INVENTION

The present invention relates to an observation that 5-[4-[[3-methyl-4-oxo-3,4-dihydroquinazolin-2-yl]methoxy] benzyl]thiazolidine-2,4-dione potassium salt exhibits polymorphism, which has not been reported till date. The crystalline Form is obtained by preparing in acetonitrile/xylene solvent, which shows melting endotherms at 296.24, 307.64° C., exotherm at 291.90° C., small exotherm at 164.23° C.

The present invention also relates to a process for the preparation of 5-[4-[[3-Methyl-4-oxo-3,4-dihydroquinazolin-2-yl]methoxy]benzyl]thiazolidine-2,4-dione potassium salt described in example 41 of our international application number PCT/US97/11522 which is being designated as Form I. Form I of 5-[4-[[3-Methyl-4-oxo-3,4-dihydroquinazolin-2-yl]methoxy]benzyl]thiazolidine-2,4-dione potassium salt has also been prepared from methanol/xylene, methanol, ethanol, isopropanol, ethyl acetate, acetone, dimethyl formamide, 1,4-dioxane, 1,4-dioxane/xylene, diethyl ketone, methylisobutylketone and DMSO and is identical and also matches with the data reported for 5-[4-[[3-Methyl-4-oxo-3, 4-dihydroquinazolin-2-yl]methoxy]benzyl]thiazolidine-2,4-dione potassium salt described in our above mentioned international application.

This novel crystalline Form was proved to be identical with the other form in solution as evident from Nuclear Magnetic Resonance (NMR), Ultra Violet (UV) & Mass spectral data. On the other hand, solid state techniques like Differential Scanning Calorimetry (DSC), Powder X-Ray Diffractometry (XRD) and Infra Red spectroscopy (IR) revealed the difference among these Forms.

BRIEF DESCRIPTION OF THE FIGURES

X-ray powder diffraction pattern has been obtained on a Rigaku D/Max 2200 model diffractometer equipped with horizontal gonimometer in $\Theta/2\Theta$ geometry. The copper K$\alpha$($\lambda$=1.5418 A) radiation was used and the sample was scanned between 3-45 degrees $2\Theta$.

Differential scanning calorimeter was performed on a Shimadzu DSC-50 equipped with a controller. The data was collected on to a Pentium PC using a Shimadzu TA-50 software. The samples weighed in aluminum cells were heated from room temperature to 350° C. at a heating rate of 10° C./min. The empty aluminum cell was used as a reference. Dry nitrogen gas was purged through DSC cell continuously throughout the analysis at a flow of 30 ml/min.

FT-IR Spectrum was recorded in solid state as KBr dispersion using Perkin-Elmer 1650 FT-IR Spectrophotometer.

FT-IR Spectrum was recorded in solid state as KBr dispersion using Perkin-Elmer 1650 FT-IR spectrophotometer.

DETAILED DESCRIPTION OF THE INVENTION

According to a feature of the present invention, there is provided a novel crystalline Form of 5-[4-[[3-methyl-4-oxo-3,4-dihydroquinazolin-2-yl]methoxy]benzyl]thiazolidine-2, 4-dione potassium salt, having the formula I

Figure 1:
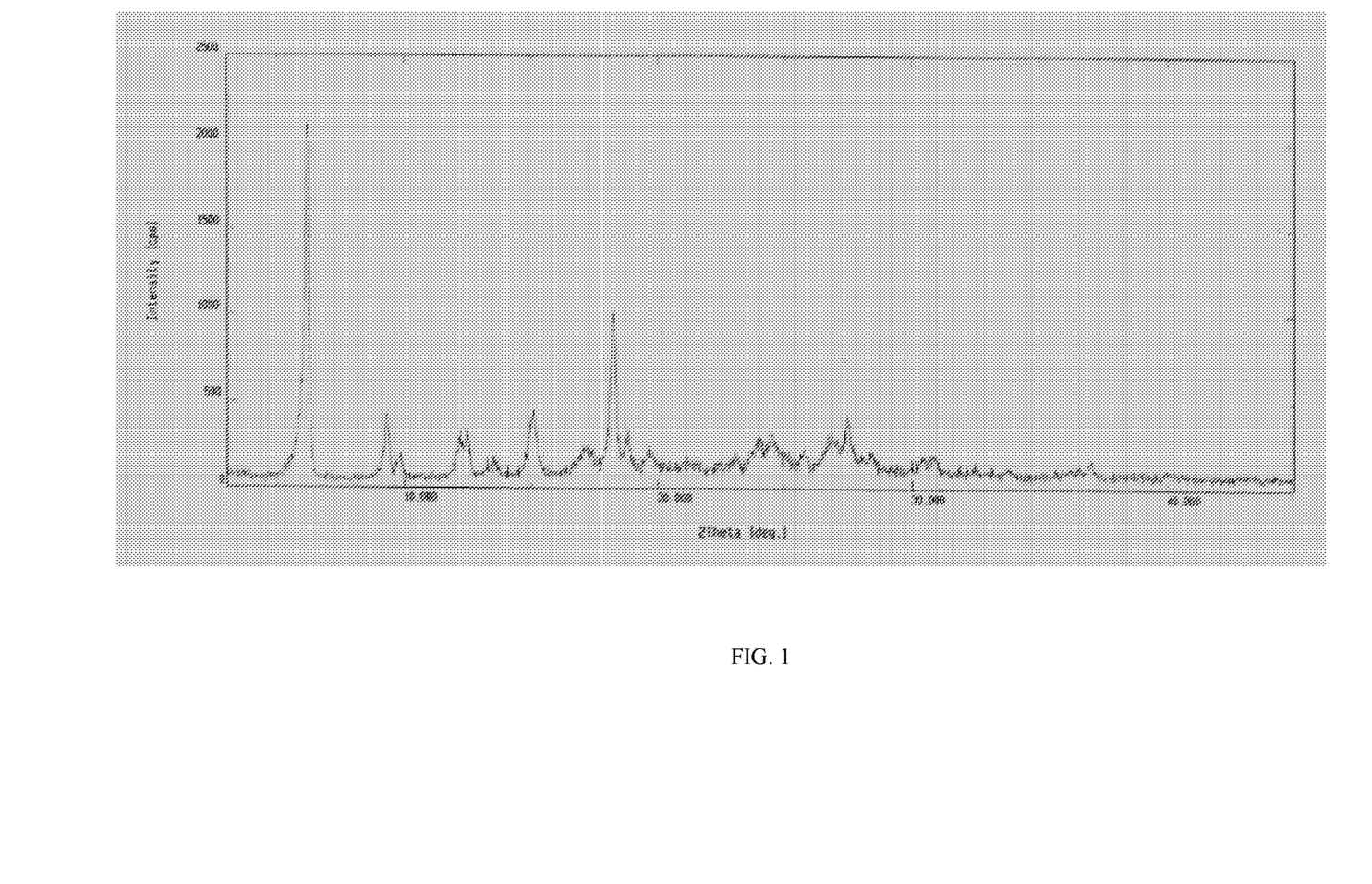
FIG. 1 is a characteristic X-ray powder diffraction pattern of novel crystalline Form.
Figure 2:
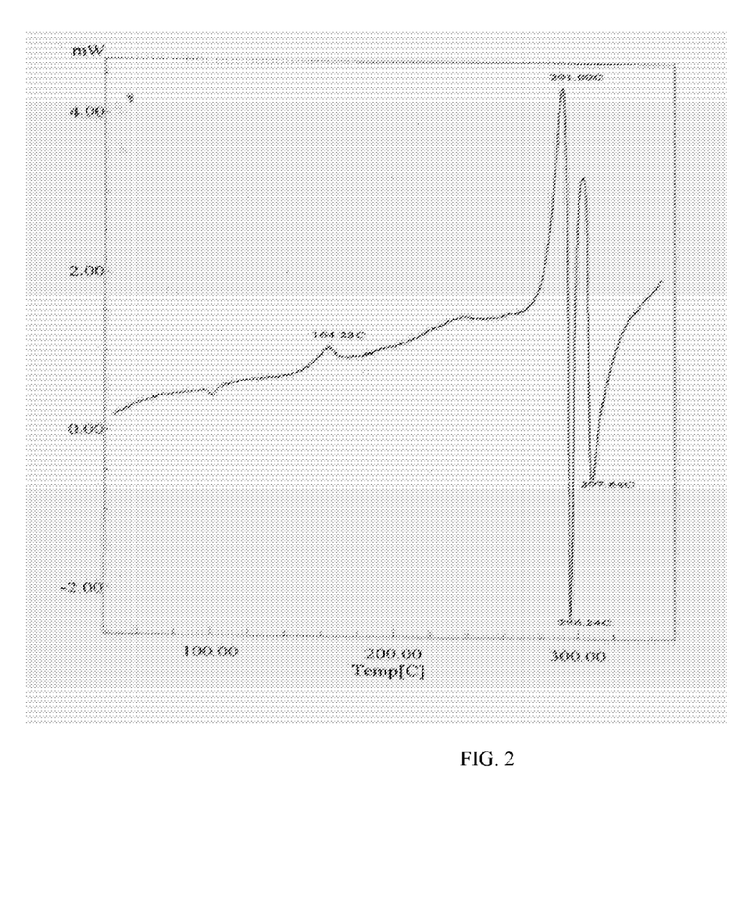
FIG. 2 is a characteristic differential scanning calorimetric thermogram of novel crystalline Form.
Figure 3:
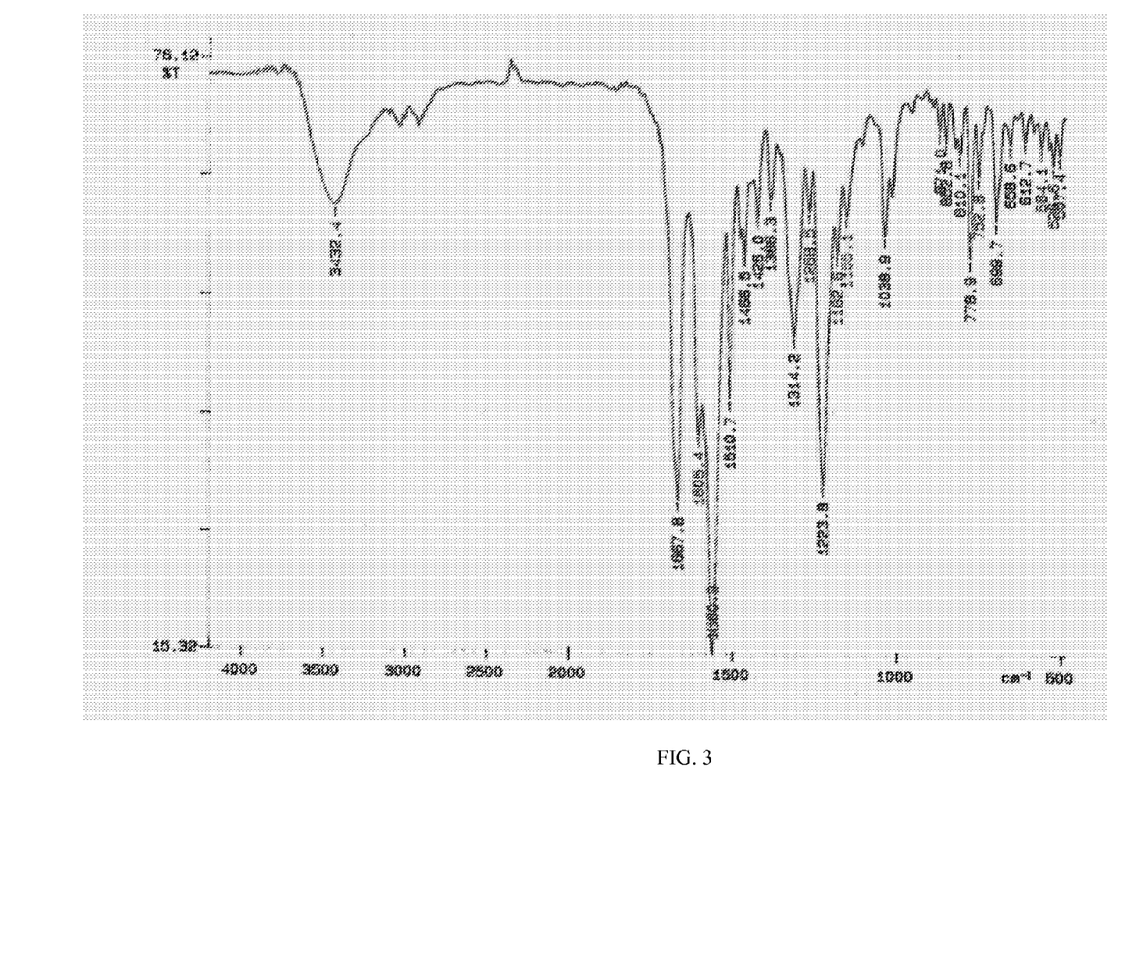
FIG. 3 is a characteristic infrared absorption spectrum of novel crystalline Form in KBr.

(I)

which is characterized by the following data:
DSC: Endotherms at 296.24, 307.64° C. (FIG. 2)
  Small exotherm at 164.23° C.
  Exotherm at 291.90° C.
IR (KBr), (cm$^{-1}$): 507.4, 564.1, 612.7, 699.7, 778.9, 810.1, 1038.9, 1223.8, 1314.2, 1426, 1466, 1510.7, 1580.9, 1667.8, 3432.4 (FIG. 3)
X-ray powder diffraction (2θ): 6.20, 9.34, 12.16, 12.48, 15.06, 18.26, 18.80, 24.02, 24.46, 26.70, 27.02, 27.48, 30.86 (FIG. 1)

According to another feature of the present invention, there is provided a process for the preparation of novel crystalline Form of 5-[4-[[3-methyl-4-oxo-3,4-dihydroquinazolin-2-yl]methoxy]benzyl]thiazolidine-2,4-dione potassium salt, of the formula I, having the characteristics described earlier, which comprises:
(i) synthesizing the 5-[4-[[3-methyl-4-oxo-3,4-dihydroquinazolin-2-yl]methoxy]benzyl]thiazolidine-2,4-dione, employing known methods and dissolving in acetonitrile and xylene mixture,
(ii) heating the resulting solution at a temperature in the range of 60-90° C. to get clear solution,
(iii) adding potassium tertiary butoxide dissolved in methanol at room temperature slowly with constant stirring to the solution obtained in step (ii),
(iv) stirring the reaction mixture at room temperature for a period in the range of 0.5-5 h to obtain precipitate,
(v) cooling the resulting solution and filtering the precipitate obtained in step (iv) above and
(vi) drying under vacuum at a temperature of 20-60° C. for a period in the range of 0.5 to 5 h to yield novel crystalline Form of 5-[4-[[3-methyl-4-oxo-3,4-dihydroquinazolin-2-yl]methoxy]benzyl]thiazolidine-2,4-dione potassium salt.

The reaction is shown in the Scheme I below:

Scheme 1

→

(I)

The present invention also envisages a pharmaceutical composition comprising a novel crystalline Form of 5-[4-[[3-methyl-4-oxo-3,4-dihydroquinazolin-2-yl]methoxy]benzyl]thiazolidine-2,4-dione potassium salt, of the formula (I) and a pharmaceutically acceptable carrier.

Figure 4:
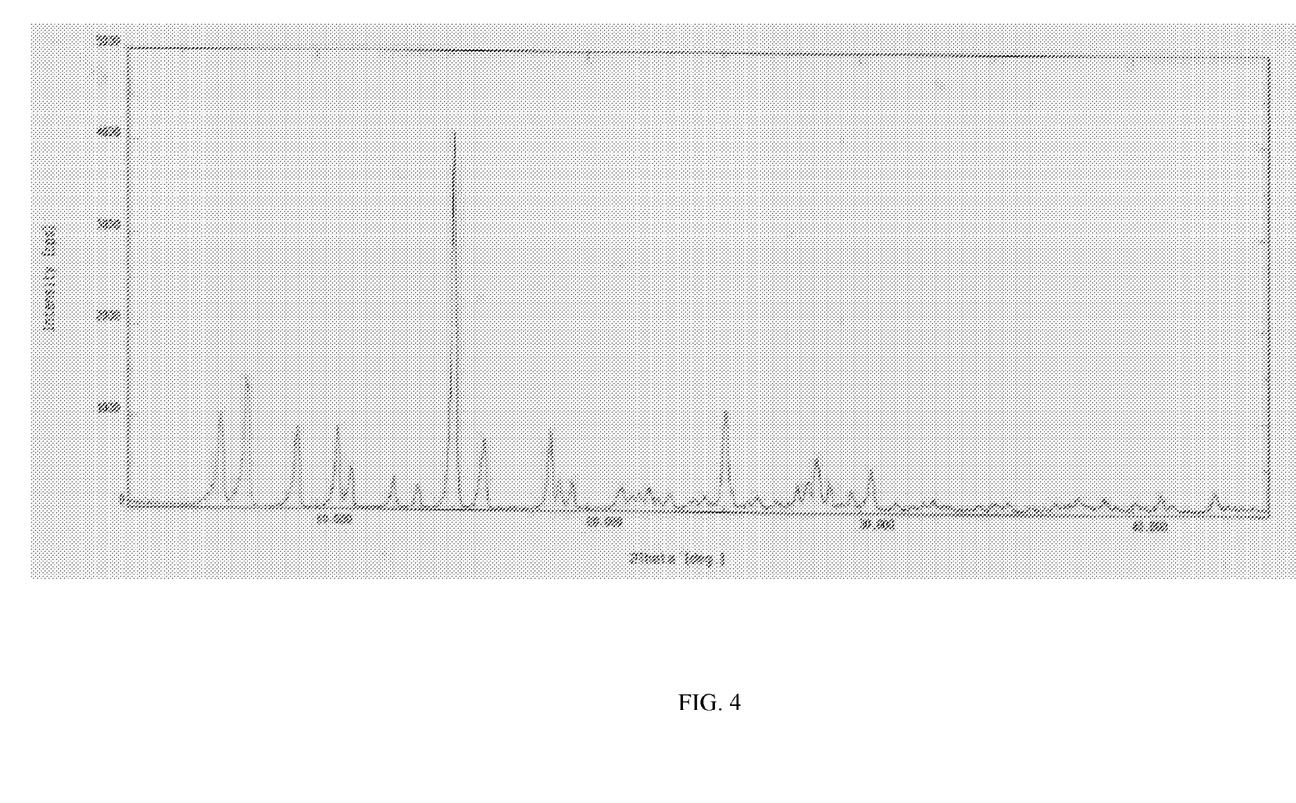
FIG. 4 is a characteristic X-ray powder diffraction pattern of novel Form-I.
Figure 5:
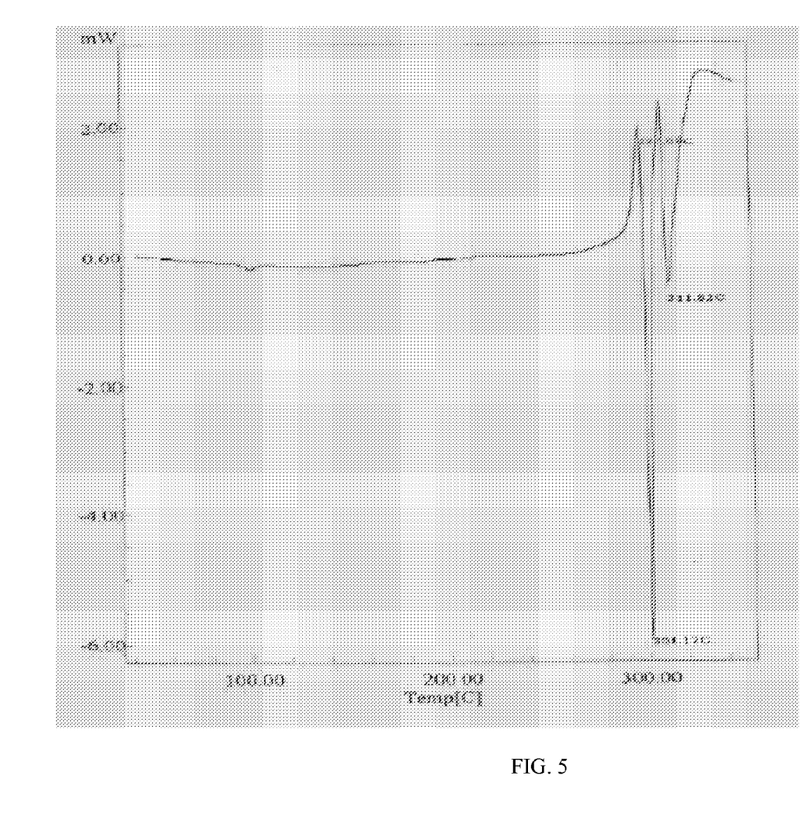
FIG. 5 is a characteristic differential scanning calorimetric thermogram of novel Form-I.
Figure 6:
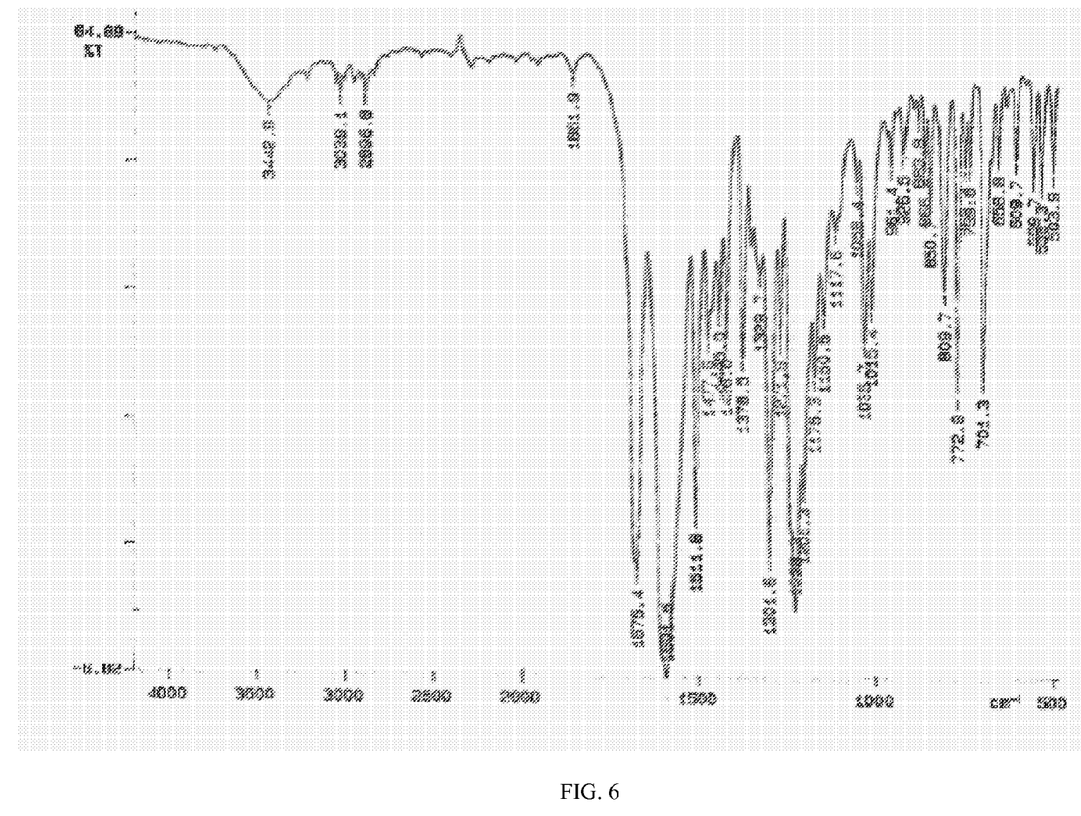
FIG. 6 is a characteristic infrared absorption spectrum of novel Form-I in KBr.

According to another embodiment of the present invention, there is provided a process for the preparation of polymorphic Form-I of 5-[4-[[3-methyl-4-oxo-3,4-dihydroquinazolin-2-yl]methoxy]benzyl]thiazolidine-2,4-dione potassium salt of the formula I, having the characteristics described
DSC: Endotherms at 301.17° C., 311.82° C. (FIG. 5)
  Exotherm at 297.68° C.
IR (KBr) (cm$^{-1}$): 503.9, 559.7, 609.7, 658.8, 609.7, 701.3, 772.9, 809.7, 1035.7, 1058.4, 1271.9, 1329.7, 1378.5, 1426, 1477.6, 1511.8, 1591.5, 1675.4, 1861.9, 3039.1, 3442.9 (FIG. 6)
X-ray powder diffraction (2θ): 6.44, 7.42, 9.28, 10.76, 11.24, 15.06, 16.16, 18.60, 25.06, 28.42, 30.40 (FIG. 4).
which comprises:
(i) synthesizing the 5-[4-[[3-methyl-4-oxo-3,4-dihydroquinazolin-2-yl]methoxy]benzyl]thiazolidine-2,4-dione, employing known methods and dissolving in an organic solvent, at 60-80° C.
(ii) adding potassium tertiary butoxide dissolved in an organic solvent at temperature 40-60° C.,
(iii) stirring the reaction mixture at a temperature of 20-90° C. for a period in the range of 1-10 h,
(iv) cooling the resulting solution and filtering the precipitate obtained in step (iii) above and
(v) drying under vacuum at a temperature of 40-70° C. for a period in the range of 1 to 6 h to yield Form-I of 5-[4-[[3-methyl-4-oxo-3,4-dihydroquinazolin-2-yl]methoxy]benzyl]thiazolidine-2,4-dione potassium salt.

The organic solvents selected from methanol, methanol and xylene mixture, acetone and xylene mixture, ethanol, isopropanol, ethyl acetate, diethyl ketone and methyl isobutyl ketone.

According to yet another embodiment of the present invention, there is provided an alternate process for the preparation of polymorphic Form-I of 5-[4-[[3-methyl-4-oxo-3,4-dihydroquinazolin-2-yl]methoxy]benzyl]thiazolidine-2,4-dione potassium salt of the formula I, having the characteristics described above, which comprises:
(i) synthesizing the 5-[4-[[3-methyl-4-oxo-3,4-dihydroquinazolin-2-yl]methoxy]benzyl]thiazolidine-2,4-dione, employing known methods and dissolving in an organic solvent, at room temperature,
(ii) adding potassium tertiary butoxide dissolved in an organic solvent at room temperature,
(iii) stirring the reaction mixture at room temperature for a period in the range of 2-20 h,
(iv) cooling the resulting solution and filtering the precipitate obtained in step (iii) above and
(v) drying under vacuum at a temperature of 40-70° C. for a period in the range of 1 to 6 h to yield Form-I of 5-[4-[[3-methyl-4-oxo-3,4-dihydroquinazolin-2-yl]methoxy]benzyl]thiazolidine-2,4-dione potassium salt.

The organic solvents selected from DMF, 1,4-Dioxane or 1,4-Dioxane and xylene mixture.

According to yet another embodiment of the present invention, there is provided an alternate process for the preparation of polymorphic Form-I of 5-[4-[[3-methyl-4-oxo-3,4-dihydroquinazolin-2-yl]methoxy]benzyl]thiazolidine-2,4-dione potassium salt of the formula I, having the characteristics described above, which comprises:

(i) synthesizing the 5-[4-[[3-methyl-4-oxo-3,4-dihydroquinazolin-2-yl]methoxy]benzyl]thiazolidine-2,4-dione potassium salt from any of the above procedure,
(ii) dissolving in DMSO at 50-80° C. to get clear solution
(iii) storing the reaction mixture at room temperature for 1-8 weeks
(iv) filtering the precipitate obtained in step (iii) above and
(v) drying under vacuum at a temperature of 40-70° C. for a period in the range of 1 to 6 h to yield Form-I of 5-[4-[[3-methyl-4-oxo-3,4-dihydroquinazolin-2-yl]methoxy]benzyl]thiazolidine-2,4-dione potassium salt.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active ingredient, the remainder of the composition being pharmaceutically acceptable carriers, diluents or solvents.

The novel crystalline Form of the formula (I) as defined above are clinically administered to mammals, including man, via either oral, nasal, pulmonary, transdermal or parenteral, rectal, depot, subcutaneous, intravenous, intraurethral, intramuscular, intranasal, ophthalmic solution or an ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the polymorphic form can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parental administration, the novel crystalline Form can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the novel crystalline Form of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder or the like are particularly suitable for any oral application. Preferably, carriers for tablets, dragees or capsules include lactose, corn starch and/or potato starch. A syrup or elixir can be used in cases where a sweetened vehicle can be employed.

A typical tablet production method is exemplified below:

Tablet Production Example:

| a) | 1) Active ingredient | 30 g |
|---|---|---|
| | 2) Lactose | 95 g |
| | 3) Corn starch | 30 g |
| | 4) Carboxymethyl cellulose | 44 g |
| | 5) Magnesium stearate | 1 g |
| | | 200 g |
| | | for 1000 tablets |

The ingredients 1 to 3 are uniformly blended with water and granulated after drying under reduced pressure. The ingredient 4 and 5 are mixed well with the granules and compressed by a tabletting machine to prepare 1000 tablets each containing 30 mg of active ingredient.

| b) | 1) Active ingredient | 30 g |
|---|---|---|
| | 2) Calcium phosphate | 90 g |
| | 3) Lactose | 40 g |
| | 4) Corn starch | 35 g |
| | 5) Polyvinyl pyrrolidone | 3.5 g |
| | 6) Magnesium stearate | 1.5 g |
| | | 200 g |
| | | for 1000 tablets |

The ingredients 1-4 are uniformly moistened with an aqueous solution of 5 and granulated after drying under reduced pressure. Ingredient 6 is added and granules are compressed by a tabletting machine to prepare 1000 tablets containing 30 mg of ingredient 1.

The invention is explained in detail in the examples given below which are provided by way of illustration only and therefore should not be construed to limit the scope of the invention.

Synthesis of 5-[4-[[3-methyl-4-oxo-3,4-dihydroquinazolin-2-yl]methoxy]benzyl]thiazolidine-2,4-dione is described in our WO publication No. WO 97/41097

EXAMPLE 1

5-[4-[[3-Methyl-4-oxo-3,4-dihydroquinazolin-2-yl]methoxy]benzyl]thiazolidine-2,4-dione (1.0 g, 0.00253M) dissolved in acetonitrile (25 ml) and xylene (7 ml) was heated to 75-80° C. to get clear solution. To this a solution of potassium tertiary butoxide (0.32 g, 0.00278M) dissolved in methanol (1 ml) was added slowly at room temperature while stirring. After complete addition, the reaction was stirred for 2 h. The precipitated product was filtered, washed with acetonitrile (1 ml) and dried under vacuum at room temperature for 1 h to yield novel crystalline Form of 5-[4-[[3-methyl-4-oxo-3,4-dihydroquinazolin-2-yl]methoxy]benzyl]thiazolidine-2,4-dione potassium salt (1.2 g)

EXAMPLE 2

5-[4-[[3-Methyl-4-oxo-3,4-dihydroquinazolin-2-yl]methoxy]benzyl]thiazolidine-2,4-dione (40 g) was dissolved in a mixture of xylene (280 ml) and methanol (280 ml) at reflux temperature to get clear solution. Potassium tertariry butoxide (12.52 g) dissolved in methanol was added slowly drop wise. After complete addition, the reaction mass was stirred at room temperature for 1 hour. The precipitated compound was filtered, washed with methanol and dried the compound in oven at 60-80° C. to yield polymorphic Form 1 of 5-[4-[[3-methyl-4-oxo-3,4-dihydroquinazolin-2-yl]methoxy]benzyl]thiazolidine-2,4-dione potassium salt (40 g).

EXAMPLE 3

5-[4-[[3-Methyl-4-oxo-3,4-dihydroquinazolin-2-yl]methoxy]benzyl]thiazolidine-2,4-dione (1.0 g) was dissolved in methanol (60 ml) at 65-75° C. to get the clear solution. A solution of potassium tertiary butoxide (0.32 g, 0.00278 M) dissolved in methanol was added slowly while stirring at 50-55° C. After complete addition, the reaction mixture was cooled to room temperature and stirred for 3 hrs. The precipitated product was filtered, washed with methanol and dried under vacuum at 60-70° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (0.85 g.)

EXAMPLE 4

5-[4-[[3-Methyl-4-oxo-3,4-dihydroquinazolin-2-yl]methoxy]benzyl]thiazolidine-2,4-dione (1.0 g) was dissolved in ethanol (60 ml) at 65-75° C. A solution of potassium tertiary butoxide (0.32 g, 0.00278 M) dissolved in ethanol was added slowly while stirring at a temperature of 50-55° C. After completion of addition, the reaction mass temperature brought down to RT and continued stirring for 3 hrs. The precipitated product was filtered, washed with ethanol and dried under vacuum at 60-70° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (0.9 g).

EXAMPLE 5

5-[4-[[3-Methyl-4-oxo-3,4-dihydroquinazolin-2-yl]methoxy]benzyl]thiazolidine-2,4-dione (1.0 g) was dissolved in isopropanol (60 ml) and heated to 65-75° C. A solution of potassium tertiary butoxide (0.32 g, 0.00278 M) dissolved in isopropanol was added slowly while stirring at 50-55° C. After complete addition, the reaction mixture was cooled to room temperature and stirred for 3 hrs. The precipitated product was filtered, washed with isopropanol and dried under vacuum at 60-70° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (1.05 g).

EXAMPLE 6

5-[4-[[3-Methyl-4-oxo-3,4-dihydroquinazolin-2-yl]methoxy]benzyl]thiazolidine-2,4-dione (1.0 g) dissolved in ethyl acetate (60 ml) at 65-75° C. A solution of potassium tertiary butoxide (0.32 g, 0.00278M.) dissolved in methanol was added slowly while stirring at 50-55° C. After complete addition, the reaction mixture was cooled to room temperature and continued stirring for 3 hrs. The precipitated product was filtered, washed with ethyl acetate and dried under vacuum at 60-70° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (1.05 g).

EXAMPLE 7

5-[4-[[3-Methyl-4-oxo-3,4-dihydroquinazolin-2-yl]methoxy]benzyl]thiazolidine-2,4-dione (2.5 g) was dissolved in a mixture of acetone (62.5 ml), xylene (17.5 ml) at 65-75° C. A solution of potassium tertiary butoxide (0.78 g, 0.00696M.) dissolved in methanol was added slowly while stirring at room temperature and continued stirring for 2 hrs. The precipitated product was filtered, washed with acetone and dried under vacuum for 1 hour to yield the polymorphic Form 1 of 5-[4-[[3-methyl-4-oxo-3,4-dihydroquinazolin-2-yl]methoxy]benzyl]thiazolidine-2,4-dione potassium salt (2.5 g).

EXAMPLE 8

5-[4-[[3-Methyl-4-oxo-3,4-dihydroquinazolin-2-yl]methoxy]benzyl]thiazolidine-2,4-dione (1.0 g) was dissolved in dimethylformamide (20 ml). A solution of potassium tertiary butoxide (0.32 g, 0.00278 M) dissolved in methanol was added slowly while stirring at room temperature. After complete addition, the reaction mixture was stirred for 14-16 hrs. The precipitated product was filtered and dried under vacuum at 60-70° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (0.15 g).

EXAMPLE 9

5-[4-[[3-Methyl-4-oxo-3,4-dihydroquinazolin-2-yl]methoxy]benzyl]thiazolidine-2,4-dione (1.0 g) was dissolved in 1,4-dioxane (25 ml). A solution of potassium tertiary butoxide (0.32 g, 0.00278 M) dissolved in methanol was added slowly at room temperature while stirring. After completion of addition, the reaction mass stirred for 3-4 hrs. The precipitated product was filtered, washed with 1,4-dioxane and dried under vacuum at 60-70° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (0.85 g).

EXAMPLE 10

5-[4-[[3-Methyl-4-oxo-3,4-dihydroquinazolin-2-yl]methoxy]benzyl]thiazolidine-2,4-dione (1.0 g) was dissolved in a mixture of 1,4-dioxane (25 ml), xylene (7.0 ml). To this, a solution of potassium tertiary butoxide (0.32 g, 0.00278 M) dissolved in methanol was added slowly at room temperature while stirring. After complete addition, the reaction mixture was stirred for 3-4 hr. The precipitated product was filtered, washed with 1,4-dioxane and dried under vacuum at room temperature for 1 hour to yield the polymorphic Form 1 of 5-[4-[[3-methyl-4-oxo-3,4-dihydroquinazolin-2-1]methoxy]benzyl]thiazolidine-2,4-dione potassium salt (0.8 g).

EXAMPLE 11

5-[4-[[3-Methyl-4-oxo-3,4-dihydroquinazolin-2-yl]methoxy]benzyl]thiazolidine-2,4-dione (1.0 g) was dissolved in diethyl ketone (60 ml) at a temperature of 75-80° C. A solution of potassium tertiary butoxide (0.32 g, 0.00278M) dissolved in methanol was added slowly at 50-60° C. while stirring. After complete addition, the reaction mixture was cooled to room temperature and continued stirring for 3-4 hrs. The precipitated product was filtered, washed with diethylketone and dried under vacuum at 60-70° C. for 2 hours to yield the polymorphic Form 1 of 5-[4-[[3-methyl-4-oxo-3,4-dihydroquinazolin-2-yl]methoxy]benzyl]thiazolidine-2,4-dione potassium salt (1.02 g).

EXAMPLE 12

5-[4-[[3-Methyl-4-oxo-3,4-dihydroquinazolin-2-yl]methoxy]benzyl]thiazolidine-2,4-dione (1.0 g) was dissolved in methyl isobutylketone (50 ml) at a temperature of 60-70° C. A solution of potassium tertiary butoxide (0.32 g, 0.00278 M) dissolved in methanol was added slowly at room temperature while stirring. After complete addition, the reaction mixture was stirred for 3-4 hrs. The precipitated product was filtered, washed with methyl isobutylketone and dried under vacuum at 65-75° C. for 1 hour to yield the polymorphic Form 1 of 5-[4-[[3-methyl-4-oxo-3,4-dihydroquinazolin-2-yl]methoxy]benzyl]thiazolidine-2,4-dione potassium salt (1.00 g).

EXAMPLE 13

5-[4-[[3-Methyl-4-oxo-3,4-dihydroquinazolin-2-yl]methoxy]benzyl]thiazolidine-2,4-dione potassium salt (0.5 g) prepared from any of the examples 2-12 as defined above, was dissolved in dimethylsulfoxide (5 ml) at 50-80° C. the resulting clear solution was stored at room temperature for 1-8 weeks. The precipitated product was filtered and dried under vacuum to yield the polymorphic Form 1 of 5-[4-[[3-methyl-4-oxo-3,4-dihydroquinazolin-2-yl]methoxy]benzyl]thiazolidine-2,4-dione potassium salt (150 mg).

Advantages Of The Invention

The polymorphic Forms of 5-[4-[[3-Methyl-4-oxo-3,4-dihydroquinazolin-2-yl]methoxy]benzyl]thiazolidine-2, 4-dione potassium salt, are more active/bioavailable and are therefore very useful for the treatment or prophylaxis.

Ease in formulation containing these forms resulting in higher activity/bioavailability, in terms of lowering plasma blood sugar and plasma triglycerides.

What is claimed is:

1. A crystalline Form of 5-[4-[[3-methyl-4-oxo-3,4-dihydroquinazolin-2-yl-]methoxy]benzyl]thiazolidine-2,4-dione potassium salt, having the formula:

wherein the crystalline compound is characterized by having an x-ray powder diffraction pattern comprising one or more peaks expressed in degrees 2θ that are selected from the group consisting of 6.20, 9.34, 12.16, 12.48, 18.26, 18.80, 24.02, 24.46, 26.70, 27.02, 27.48, and 30.86± about 0.1.

2. A process for preparing the crystalline Form of 5-[4-[[3-methyl-4-oxo-3,4-dihydroquinazolin-2-yl-]methoxy]benzyl]thiazolidine-2,4-dione potassium salt, having the formula:

wherein the crystalline compound is characterized by having an x-ray powder diffraction pattern comprising one or more peaks expressed in degrees 2θ that are selected from the group consisting of 6.20, 9.34, 12.16, 12.48, 18.26, 18.80, 24.02, 24.46, 26.70, 27.02, 27.48, and 30.86± about 0.1, comprising:
  (i) heating 5-[4-[[3-methyl-4-oxo-3,4-dihydroquinazolin-2-yl]methoxy]benzyl]thiazolidine-2,4-dione in a mixture of acetonitrile and xylene to a temperature in the range of 60-90° C.;
  (ii) cooling the solution of step (i) to about room temperature;
  (iii) at about room temperature, adding potassium tertiary butoxide dissolved in methanol to the solution of step (i);
  (vi) recovering the crystalline form of 5-[4-[[3-methyl-4-oxo-3,4-dihydroquinazolin-2-yl ]methoxy]benzyl]thiazolidine-2,4-dione potassium salt.

3. The crystalline Form of claim 1, wherein said compound comprises five or more of said x-ray powder diffraction peaks.

4. The crystalline Form of claim 1, wherein said compound comprises all of said x-ray powder diffraction peaks.

* * * * *